United States Patent
Graf et al.

(10) Patent No.: US 10,258,812 B2
(45) Date of Patent: Apr. 16, 2019

(54) RADIATION TREATMENT SYSTEMS

(71) Applicant: Varian Medical Systems, Inc., Palo Alto, CA (US)

(72) Inventors: Andres Graf, Oberwil (CH); Hanspeter Felix, Zofingen (CN); Qingxiang Ke, San Jose, CA (US); Angi Ye, Milpitas, CA (US)

(73) Assignee: Varian Medical Systems, Inc., Palo Alto, CA (US)

( * ) Notice: Subject to any disclaimer, the term of this patent is extended or adjusted under 35 U.S.C. 154(b) by 832 days.

(21) Appl. No.: 14/631,617

(22) Filed: Feb. 25, 2015

(65) Prior Publication Data

US 2015/0165236 A1   Jun. 18, 2015

Related U.S. Application Data

(63) Continuation of application No. 13/086,338, filed on Apr. 13, 2011, now Pat. No. 8,992,404.

(60) Provisional application No. 61/323,859, filed on Apr. 13, 2010.

(51) Int. Cl.
   *A61N 5/10*   (2006.01)

(52) U.S. Cl.
   CPC ......... *A61N 5/1048* (2013.01); *A61N 5/1045* (2013.01); *A61N 5/1049* (2013.01); *A61N 2005/1061* (2013.01)

(58) Field of Classification Search
   None
   See application file for complete search history.

(56) References Cited

U.S. PATENT DOCUMENTS

| | | | |
|---|---|---|---|
| 6,865,254 B2 | 3/2005 | Nafstadius | |
| 7,397,054 B2 | 7/2008 | Natori et al. | |
| 7,847,274 B2 | 12/2010 | Kornblau et al. | |
| 8,300,685 B2 | 10/2012 | Chen et al. | |

(Continued)

FOREIGN PATENT DOCUMENTS

| | | |
|---|---|---|
| CN | 100586507 | 2/2010 |
| KR | 10-2001-0097505 | 11/2001 |

(Continued)

OTHER PUBLICATIONS

International Search Report and Written Opinion in PCT/US2011/032327, dated Dec. 27, 2011, 13 pages.

(Continued)

*Primary Examiner* — Christine H Matthews
*Assistant Examiner* — Joshua Daryl D Lannu
(74) *Attorney, Agent, or Firm* — Kilpatrick Townsend & Stockton LLP

(57) ABSTRACT

Disclosed are radiation treatment systems with enhanced control architectures that enable more complex treatment plans to be implemented, and radiation treatment systems with enhanced resistance to the effect of neutrons. An exemplary control architectures comprises: a digital packet network; a supervisor electrically coupled to the digital packet network and having a treatment plan; and a plurality of nodes, each node coupled to digital packet network and controlling one or more treatment-related components of the radiation treatment system; and wherein the supervisor periodically communicates control orders to the nodes over the digital packet network.

20 Claims, 9 Drawing Sheets

(56) References Cited

U.S. PATENT DOCUMENTS

| | | |
|---|---|---|
| 8,300,907 B2 | 10/2012 | Nagamine et al. |
| 8,384,054 B2 | 2/2013 | Fehrenbacher et al. |
| 2004/0174958 A1 | 9/2004 | Moriyama et al. |
| 2005/0259779 A1* | 11/2005 | Abraham-Fuchs .......... A61N 5/1048 378/2 |
| 2008/0069303 A1 | 3/2008 | Kim |
| 2008/0203323 A1 | 8/2008 | Fehrenbacher |
| 2008/0237494 A1 | 10/2008 | Beloussov et al. |
| 2009/0161818 A1 | 6/2009 | Sakurai et al. |
| 2010/0231962 A1 | 9/2010 | Sakai et al. |

FOREIGN PATENT DOCUMENTS

| | | |
|---|---|---|
| KR | 10-2009-0119241 | 11/2009 |
| WO | 2007/014027 | 2/2007 |
| WO | 2007/014109 | 2/2007 |

OTHER PUBLICATIONS

Search Report dated Jun. 2, 2014 in European Patent Application No. 11769529, 16 pages.

* cited by examiner

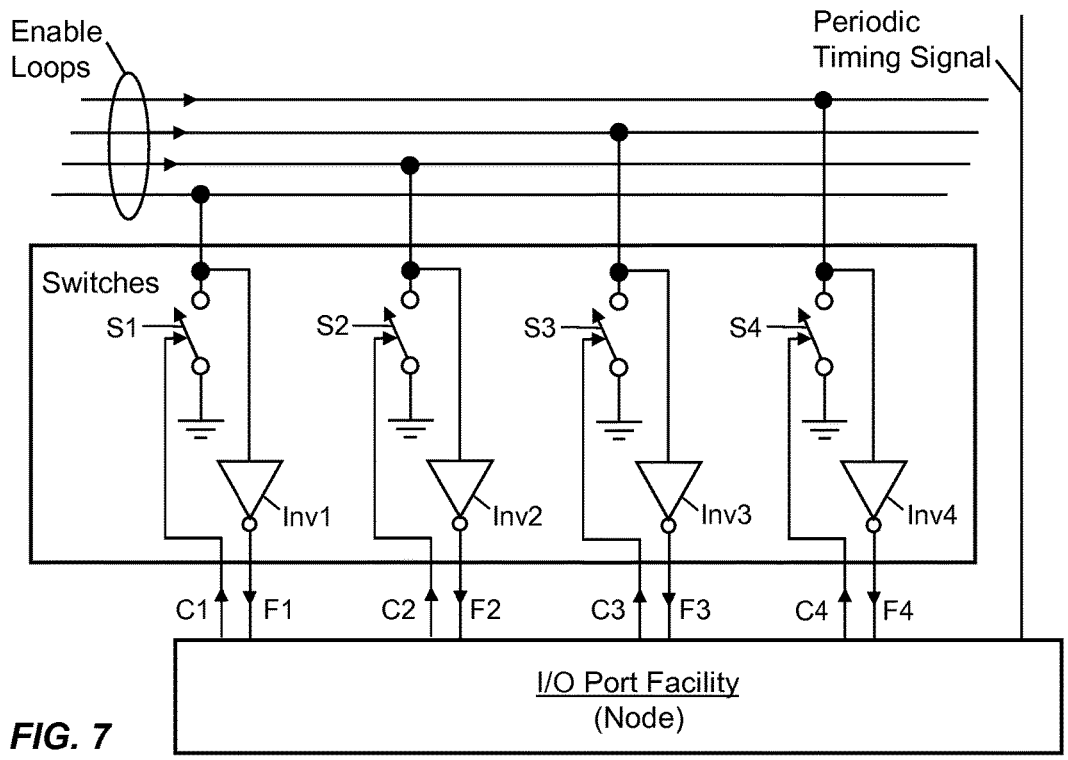

FIG. 7

| First Command to an Example Node |
|---|
| Action Order(s) for time point T1 |
| Action Order(s) for time point T2 |
| Action Order(s) for time point T3 |

FIG. 8A

| Second Command to an Example Node |
|---|
| Action Order(s) for time point T2 |
| Action Order(s) for time point T3 |
| Action Order(s) for time point T4 |

FIG. 8B

| Third Command to an Example Node |
|---|
| Action Order(s) for time point T3 |
| Action Order(s) for time point T4 |
| Action Order(s) for time point T5 |

FIG. 8C

| Error Message to Supervisor from Node |
|---|
| Did not receive Action Order(s) for time point T2 |

FIG. 9A

| Error Message to Supervisor from Node |
|---|
| Did not receive Action Order(s) for time point T3 |

FIG. 9B

RADIATION TREATMENT SYSTEMS

CROSS-REFERENCE TO RELATED APPLICATIONS

This application is a continuation of application Ser. No. 13/086,338, filed Apr. 13, 2011, entitled "RADIATION TREATMENT SYSTEMS," which claims priority to Application No. 61/323,859, filed Apr. 13, 2010, the contents of which are hereby incorporated in their entirety by reference for all purposes.

BACKGROUND

Radio-surgery is a medical procedure that allows non-invasive treatment of benign and malignant tumors. It is also known as stereotactic radiotherapy (SRS) when used to target lesions in the brain, and stereotactic body radiotherapy (SBRT) when used to target lesions in the body. In addition to cancer, it has also been shown to be beneficial for the treatment of some non-cancerous conditions, including functional disorders such as arteriovenous malformations (AVM's) and trigeminal neuralgia. It operates by directing highly focused beams of ionizing radiation (e.g., X-rays, gamma rays) with high precision. It was initially developed in 1951, and can be used to ablate, by means of a precise dosage of radiation, intracranial and extracranial tumors and other lesions that are inaccessible using ordinary surgery techniques. There are many nerve diseases for which conventional surgical treatment is difficult or inadvisable, or have deleterious consequences, such as damage to nearby arteries, nerves, and other vital structures.

A linear accelerator (LINAC) may be used to deliver radio-surgery. LINAC-based radio-surgery was pioneered at the University of Florida College of Medicine and introduced by Betti and Colombo in the mid-1980s. Modern LINACs optimized for radio-surgery applications include the Trilogy machine from Varian Medical Systems, and the Novalis Tx radiosurgery platform, produced by Varian and BrainLAB. These systems differ from the Gamma Knife in a variety of ways. The Gamma Knife produces gamma rays from the decay of Co-60 of an average energy of 1.25 MeV. A LINAC produces X-rays from the impact of accelerated electrons striking a metal target (usually tungsten). A LINAC therefore can generate any number of energy x-rays. The Gamma Knife has over 200 sources arrayed in the helmet to deliver a variety of treatment angles. On a LINAC, the gantry moves in space to change the delivery angle. Both can move the patient in space to also change the delivery point. Both systems preferably use a stereotactic frame to restrict the patient's movement, although a frame is not needed on the Varian Trilogy and the Novalis Tx radiosurgery platform. The Varian Trilogy can also be used with non-invasive immobilization devices coupled with real-time imaging to detect any patient motion during a treatment.

While the LINAC systems provide many advantages, they are much more complex to control. For example, as the gantry rotates about the patient, the jaws and leaves of the collimator must be varied, and the signals to the linear accelerator must be varied, to implement a desired radiation dosage plan. This complexity limits the ability to implement certain types of treatment plans.

BRIEF SUMMARY

One invention of the present application encompasses radiation treatment systems that have enhanced control architectures that enable more complex treatment plans to be implemented. Broadly stated, an exemplary system comprises: a plurality of treatment-related components; a digital packet network; a supervisor control entity electrically coupled to the digital packet network and having a treatment plan; and a plurality of nodes, each node coupled to a digital packet network and controlling one or more components of the radiation treatment system; and wherein the supervisor periodically communicates control orders to the nodes over the digital packet network. As used herein, the term "radiation" encompasses all forms of particle and electromagnetic radiation, including, but not limited to: ionizing radiation, non-ionization radiation, electron beams, proton beams, ion beams, atom beams, microwave beams, radio-frequency beams, etc.

Another invention of the present application encompasses control systems for radiation treatment systems. Broadly stated, an exemplary control system comprises: a digital packet network; a supervisor control entity electrically coupled to the digital packet network and having a treatment plan; and a plurality of nodes, each node being coupled to the digital packet communications network and controlling one or more components of its host system; and wherein the supervisor periodically communicates commands to the nodes over the digital packet communications network.

Yet another invention of the present application encompasses radiation treatment systems that have increased ability to withstand interfering effects from scatter neutron and other forms of radiation. Broadly stated, an exemplary system comprises: a plurality of treatment-related components; a digital packet network; a supervisor control entity electrically coupled to the digital packet network and having a treatment plan; and a plurality of nodes, each node coupled to the digital packet communications network and controlling one or more treatment-related components; and wherein a plurality of treatment-related components are disposed within a treatment room, and wherein the supervisor control entity and at least one node are disposed outside of the treatment room.

Yet another invention of the present application encompasses radiation treatment systems that have increased ability to withstand interfering effects from scatter neutron and other forms of radiation. Broadly stated, an exemplary system comprises: a plurality of treatment-related components; a digital packet network; a supervisor control entity electrically coupled to the digital packet network and having a treatment plan; a plurality of nodes, each node coupled to the digital packet communications network and controlling one or more treatment-related components; and a body of neutron-absorbing material disposed between at least one treatment-related component and the supervisor, the body of neutron-absorbing material reducing the neutron flux density passing through itself by a factor of ten or more.

Yet another invention of the present application encompasses radiation treatment systems that have increased ability to withstand interfering effects from scatter neutron and other forms of radiation. Broadly stated, an exemplary system comprises: a plurality of treatment-related components; a digital packet network; a supervisor control entity electrically coupled to the digital packet network and having a treatment plan; a plurality of nodes, each node coupled to the digital packet communications network and controlling one or more treatment-related components; and a body of neutron-absorbing material disposed between at least one treatment-related component and the supervisor, the body of neutron-absorbing material absorbing neutrons to a greater degree than gypsum.

Yet another invention of the present application encompasses radiation treatment systems that have increased ability to withstand interfering effects from scatter neutron and other forms of radiation. Broadly stated, an exemplary system comprises: a plurality of treatment-related components; and a plurality of nodes, each node controlling one or more treatment-related components, wherein at least one node comprises at least one sub-node, wherein the at least one sub-node controls at least one aspect of a treatment-related component and receives directions from the at least one node, wherein the at least one sub-node comprises a processor, a flash memory, a volatile memory, and a parameter stored at three or more different locations in the volatile memory.

The above inventions and additional embodiments thereof are described in the Detailed Description with reference to the Figures. In the Figures, like numerals may reference like elements and descriptions of some elements may not be repeated.

BRIEF DESCRIPTION OF THE DRAWINGS

FIG. 7 shows another exemplary node switch block according to the present invention.

FIGS. 8A-8C show exemplary commands sent from the supervisor to an exemplary node according to the present invention.

FIGS. 9A-9B show exemplary error message sent from the exemplary node to the supervisor according to the present invention.

DETAILED DESCRIPTION OF THE INVENTION

Figure 1:
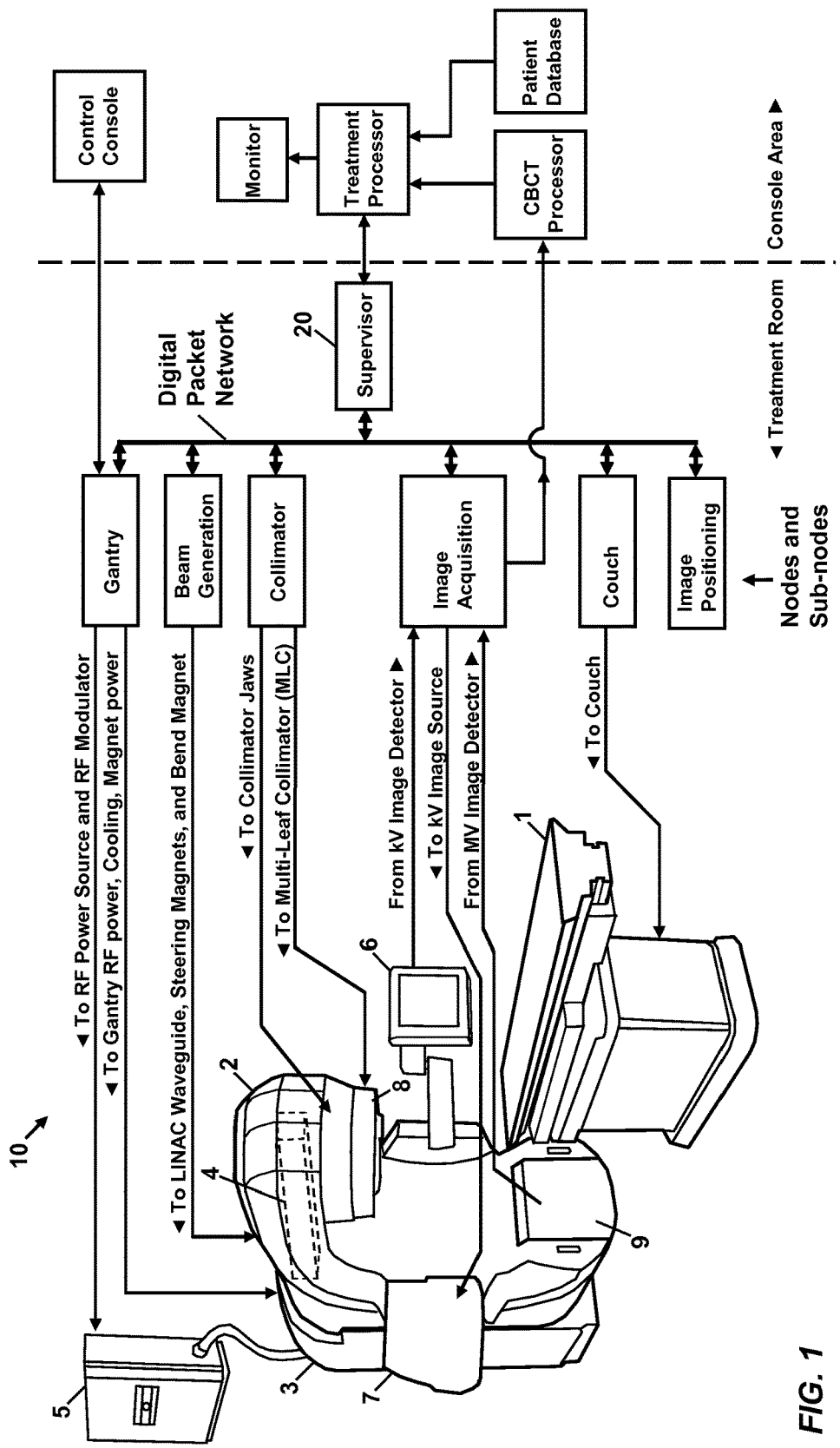
FIG. 1 shows an exemplary radiation treatment system according to the present invention.

FIG. 1 shows an exemplary radiation treatment system 10 with an exemplary control system according to the present invention. Like the Varian Trilogy system, the exemplary embodiment comprises a patient support (e.g., patient couch) 1 that can move the patient, a gantry 2 that circles about one end of the patient couch, a stand 3 that supports the gantry, a beam generator 4 mounted in the gantry, an radio-frequency (RF) power source and RF modulator 5 that feed power to beam generator 4, a first image detector 6 mounted to the gantry, and a first imaging radiation source 7 mounted to the gantry opposite to first image detector 6. Beam generator 4 comprises a linear accelerator that generates and accelerates electrons into a beam of electrons, a "bend" magnet that bends the electron beam by 270 degrees (resulting in an effective 90 degree turn), and a tungsten target, which can be selectively used depending upon the patient's treatment plan. When the tungsten target is used, the electron beam generated by the linear accelerator strikes the target and generates X-rays, which are conveyed to the patient treatment area, as described below. When the tungsten target is not used, the electron beam is conveyed to the patient treatment area. The linear accelerator has an electron gun, an accelerating structure of electrode chambers about a meter in length, and a magnetron or klystron that generates microwave pulse signals for the electrodes of the accelerating structure. The electrons from the accelerator or the X-rays generated by the target are spatially filtered by an adjustable multi-leaf collimator (MLC) 8 having a plurality of moveable leaves of radiation-absorbent material (e.g., 120 leaves). A treatment beam of electrons or X-Rays emerges from MLC 8, and the beam can have a wide range of cross-sectional patterns, as set by the positions of the leaves of MLC 8. Prior to reaching MLC 8, the treatment beam is passed through a set of jaws, which open and close around the beam. When the jaws are closed, the treatment beam does not emerge from the collimator structure. When the jaws are open, the treatment beam emerges and strikes the patient. The first imaging detector and imaging radiation source lie in a plane that is perpendicular to the treatment beam. The treatment system may also comprise a second imaging detector 9 disposed about 6 feet away and opposite to the treatment beam (in FIG. 1, this second imaging detector is shown in a folded position, folded into a compartment of the gantry). The second imaging detector uses radiation from the treatment beam to provide an image that is perpendicular to that provided by the first imaging detector.

Patient support 1 need not be moveable, and may be a fixed support. Gantry 2 and stand 3 implement one particular form of a beam-positioning mechanism that is capable of holding and/or moving the radiation beam path (e.g., trajectory) with respect to the patient. Other beam-positioning mechanisms are known to the art, and may be used in conjunction with the invention. Beam-positioning mechanisms include, but are not limited to: gantries, ring gantries, robotic arms, beam-steering devices (including those that use electric fields and/or magnetic fields), and combinations thereof. Multi-leaf collimator 8 implements one particular form of a beam-shaping mechanism that is capable of modifying the cross-sectional shape of the radiation beam. Beam-shaping devices include, but are not limited to, multi-leaf collimators, iris collimators, jaw collimators, electric-field shapers (e.g., "electrostatic" shapers), magnetic-field shapers (e.g., "magnetic" lenses), and combinations thereof. Beam-positioning mechanisms, beam-shaping mechanisms, patient support 1, gantry 2, stand 3, beam generator 4, RF modulator 5, image detector 6, imaging radiation source 7, multi-leaf collimator (MLC) 8, the collimator jaws, and the second imaging detector 9 are referred to herein as treatment-related components of radiation treatment system 10 to distinguish them from the components of the novel control systems of the present invention, described below in greater detail. A radiation treatment system encompassed by the present invention need not have all of the above-listed components, but may have any number of components and any type of components, as appropriate for the particular treatment being performed by the system.

A radiation treatment plan comprises a coordination of the movements of the gantry, patient support, and leaves of the MLC, along with coordinated adjustments to the energy level and dosage of the X-rays or other radiation produced by the beam generator. The plan is designed to provide a certain dosage of radiation to a tumor located in the patient's body, while minimizing the amount of radiation received by the surrounding healthy tissue. The gantry moves the X-ray beam around the patient to minimize the impact on healthy tissue, while still aiming the beam to go through the tumor. The positions of the leaves of the MLC are moved so as to shape the cross section of the X-ray beam to be near or within the cross-section of the tumor at the particular position of the gantry. The entire MLC may be rotated as well, providing another degree of motion control. The imaging system (e.g., the two imaging detectors) can be used to align the system to the patient's tumor, such as by using the images from the detectors to determine how to move the patient support to align the MLC to the tumor. Software tools are available to devise a treatment plan for any given tumor size and location. The output of such a software tool may be imported into the system shown in FIG. 1 and used. Accordingly, in broad terms, a radiation treatment plan comprises a coordination of the operations of two or more radiation treatment components of the radiation treatment system, where such operations may include, but are not limited to, positions, movements, and parameter settings (e.g., energy, dosages, etc).

As a difference with prior LINAC systems, the embodiment of the invention shown in FIG. 1 comprises a novel and inventive distributed control system that coordinates the operation of the components shown in the figure, such as the gantry (stand), beam generator, MLC collimator, patient support, and the imaging system. The control system comprises a supervisor 20, a plurality of nodes, each of which can have one or more sub-nodes, for a total of a plurality of sub-nodes. The nodes are identified with the following labels in FIG. 1: "Gantry," "Beam Generation," "Collimator," "Image Acquisition," "Couch," and "Image Positioning." The supervisor and the nodes are electrically coupled to one another by a digital-packet network, such as a local Ethernet (e.g., LAN). The supervisor periodically communicates instructions to the nodes, and periodically receives status information from the nodes. Each node handles the operation of one or more components of the system. For example, the Gantry node may direct the operation of the gantry, the Collimator node may direct the operation of the leaves, jaws, and rotation angle of the collimator, the Couch node may control the operation of the patient support, the Beam Generation node may control the operation of the beam generator (including the linear accelerator and the bend magnet that bends the beam 90 degrees), and an Image Acquisition node may control one or both of the two imaging systems. Each node may control one or more sub-nodes. For example, the Beam Generation node may have a first sub-node that controls the electron gun, a second sub-node that controls the magnetron or klystron, and a third node that controls the bend magnet.

Figure 2:
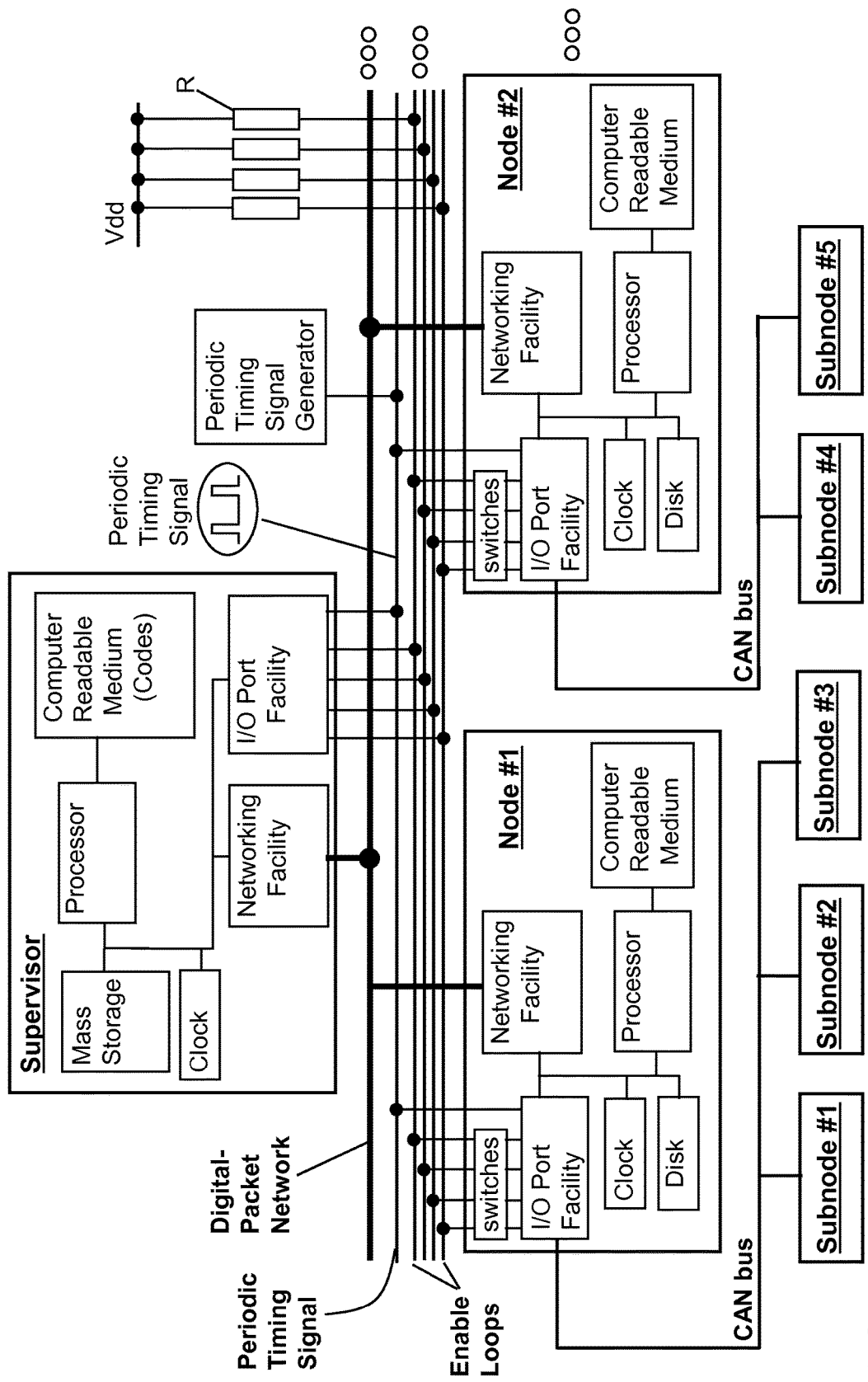
FIG. 2 shows an exemplary control system according to the present invention.

Referring to FIG. 2, the supervisor comprises a data processor, a tangible non-transitory computer-readable memory electrically coupled to the data processor for storing data and instructions (e.g. codes), a networking facility electrically coupled to the data processor and to the digital-packet network, a clock electrically coupled to the data processor, an I/O port facility electrically coupled to the data processor, and tangible non-transitory computer-readable mass storage element electrically coupled to the data processor (e.g., magnetic storage disk or flash drive). Each node comprises a data processor, a tangible non-transitory computer-readable memory electrically coupled to the data processor for storing data and processor instructions (e.g. codes), a networking facility electrically coupled to the data processor and to the digital-packet network, a clock electrically coupled to the data processor, and an I/O port facility electrically coupled to the data processor, and may comprise a tangible non-transitory computer-readable mass storage element electrically coupled to the data processor (e.g., magnetic storage disk or flash drive). The supervisor may provide a periodic timing signal on one or more lines of one of its I/O ports, and this periodic timing signal may be electrically coupled to one or more corresponding lines of an I/O port of each node. The periodic timing signal can be used to synchronize the operation of the nodes to the operation of the supervisors. As another approach, the periodic timing signal can be provided by a periodic timing signal generator, as shown in FIG. 2, in which case the I/O port of the supervisor may receive the periodic timing signal and use it to coordinate its instructions to the nodes. The processor of each node may be directed by instructions stored in the computer-readable memory to configure the I/O port facility to generate a processor interrupt signal to the data processor when the periodic timing signal is received at the I/O port. In response to receiving an interrupt signal, the data processor may be directed by instructions to perform one or more tasks (action orders) previously sent to it by the supervisor, and to send status information back to the supervisor. As yet another approach, the periodic timing signal can be broadcast on the digital-packet network by the supervisor or periodic timing signal generator as periodic general broadcast packets. Each node may comprise an internal periodic signal generator and may synchronize its internal generator according to the time of the received packet having the external periodic timing signal. In this way, if a node misses the packet of the external periodic timing signal, it may rely upon its internal clock to set the timing of the action orders that it is to perform according to the commands that it has received from the supervisor.

If a node has one or more sub-nodes under its control, then lines of its one or more I/O ports are coupled to the sub-nodes, such as through a CAN bus (Control Area Network Bus). Each sub-node may comprise digitally-controlled circuitry, or may comprise the same components as a node, depending upon the tasks to be performed by the sub-node.

In typical implementations, the system provided by the supervisor, nodes, and sub-nodes provides real-time status information to the supervisor for over 140 "mechanical parameters," where a mechanical parameter is a generic term used herein to cover the position of an element (such as a collimator leaf), the axial position of an element (such as the rotation angle of the gantry), the dose output of the accelerator's electron gun, the energy of the accelerator's electron beam, and the strength of the bend magnet. (The term "mechanical axes" is also used herein to denote these generic mechanical parameters.) The system also provides real-time control over each of the mechanical parameters (or mechanical axes) by the supervisor and nodes. The system also provides real-time status for several tens of electrical sensors to the supervisor, real-time control of multiple static and dynamic magnetic fields (which may be viewed as "mechanical parameters"), collection of imaging data from zero to several flat panel X-Ray detectors, and collection of imaging data from zero or more optical imaging cameras. In this context, "real time" means controlling all axes and magnetic fields within approximately 30 mSec of having received status information from all the axes and/or electrical sensors.

Another inventive aspect of the present application pertains to the commands sent to the nodes by the supervisor. The supervisor periodically sends commands, in the form of data packets on the digital packet network, to the nodes, such as every 10 mSec (milliseconds). These data packets can be sent just after the periodic timing signal issues an active pulse at the I/O ports of the nodes. Each command provides a first action order to the node specifying the task(s) the node is to perform at the receipt of the next active pulse of the periodic timing signal, and a second action order to the node specifying the task(s) the node is to perform at the receipt of the second next active pulse of the periodic timing signal. For example, if the supervisor issues command packets to all of the nodes at time=10 mSec (all of the commands can be sent and received on the digital packet network within about 1 mSec), then each command has action orders for the task(s) the node is to do at time=20 mSec, and for the task(s) the node is to do at time=30 mSec. Thus, if the node does not receive a command, it still has a redundant back-up action order provided in the last command it received from the supervisor. A command may provide orders for subsequent time points as well, such as a third action order specifying the task(s) the node is to perform at the receipt of the third next active pulse of the periodic timing signal. Each node monitors the incoming commands and detects if a command has not arrived when expected. If a command is missing, its contents will have been covered by the previous command (and possibly subsequent commands). If two successive commands are missing, the node can assert a communication failure fault indication through one or both of the following communication paths: a message packet to the supervisor sent via the digital-packet network, and opening one of the enable loops, as described below.

The above redundancy concepts are illustrated now with some examples for an exemplary node where actions are to be conducted at period points in time T1, T2, T3, T4 etc. Before the first time point T1, the exemplary node receives a first command from the supervisor having a first action order for the first time point T1 and a second action order for the second time point T2, the second time point T2 being later in time (e.g., subsequent) to the first time point T1. The first command, which is illustrated in FIG. 8A, may optionally have a third action order for the third time point T3, which is subsequent in time to both T2 and T1. The node executes the action specified in the first action order it received in the first command substantially when the first time point T1 occurs (e.g., within a few milliseconds of T1, or within 20% of the time interval between T1 and T2), and saves the second action order (and optionally the third action order) for possible later use. The exemplary node then waits for a second command to arrive after the first command has been received, and before the second time point T2 is to occur. If the exemplary node does not receive a second command within a selected period of time before the second time point T2, such as within 1 millisecond of T2, it proceeds to execute the action specified in the second action order that it received in the first command substantially when the second time point T2 occurs, and sends an error message packet (shown in FIG. 9A) to the supervisor over the digital-packet network indicating that it did not receive a command when it should have received one.

If, instead, the exemplary node received a second command from the supervisor within the selected period of time before the second time point T2, then the exemplary node acts on the second command. The second command has a second action order for the second time point T2 and a third action order for the third time point T3, the third time point T3 being later in time (e.g., subsequent) to the second time point T2 and the first time point T1. The second command, which is illustrated in FIG. 8B, may optionally have a fourth action order for the fourth time point T4, which is subsequent in time to each of time points T1-T3. The exemplary node can erase the stored portions of the first command after it receives the second command. The node then executes the action specified in the second action order it received in the second command substantially when the second time point T2 occurs (e.g., within a few milliseconds of T2, or within 20% of the time interval between T2 and T3), and saves the third action order (and optionally the fourth action order) for possible later use. The exemplary node then waits for a third command to arrive after the second command has been received, and before the third time point T3 is to occur. If the exemplary node does not receive a third command within a selected period of time before the third time point T3, such as within 1 millisecond of T3, it proceeds to execute the action specified in the second action order that it received in the second command substantially when the third time point T3 occurs, and sends an error message packet to the supervisor over the digital-packet network indicating that it did not receive a command when it should have received one. If the second command was not received, and if the first command contained a third action order for T3, then the exemplary node proceeds to execute the action specified in the third action order that it received in the first command substantially when the third time point T3 occurs, and sends an error message packet (shown in FIG. 9B) to the supervisor over the digital-packet network indicating that it did not receive a command when it should have received one.

If, instead, the exemplary node received a third command from the supervisor within the selected period of time before the third time point T3, then the exemplary node acts on the third command in a manner similar to how it acted on the first and second commands. The node processes subsequent commands in a similar manner. If the node does not have an action order to act on for a specific point in time, it may take a selected course of failsafe action, dependent upon the components it controls.

Referring to FIG. 2, the system can have one or more "enable loops" that provide for safety of operation (e.g., provide for single-fault safety or single-fault failsafe capability). Four enable loops are shown in FIG. 2. Each enable loop may pertain to a different safety concern and/or control concern. An enable loop may go to each node or may pass through each node of the system, or only those nodes of the system which may detect a fault that is relevant to the concerns(s) pertaining to the control loop, or which may need to react to a fault condition detected by the enable loop. The system can have the following four enable loops: (1) a beam enable loop which pertains to the beam generation; (2) a motion enable loop which pertains to the motions of the gantry, collimator, imaging arms, and patient support, (3) a power enable loop which pertains to powering those components that may become hazardous to the patient if uncontrolled (such as motors, pumps, high current power supplies, etc.), and (4) an imaging beams enable loop which pertains to the low energy X-ray beams used for imaging. A node may be coupled to one or more of these loops, and may trigger faults on the loops based on different criteria.

In one implementation, each loop may comprise an electrical signal wire that starts at an output line of an I/O port of the supervisor (or a resistor R coupled to a voltage supply Vdd), and goes through one or more electronic switches of one or more corresponding nodes, and returns back to an input line of a I/O port of the supervisor. When a node sees no operating faults, it commands its electronic switch to the closed position, which completes the electrical loop from the output line of the supervisor (or a resistor R coupled to a voltage supply Vdd) to the input line of the supervisor. When a node sees an operating fault, it commands its electronic switch to the open position, which breaks the electrical loop and changes the voltage at the input line of the supervisor. The supervisor monitors the input line for a voltage level indicative of a break, which signals a fault condition. A node can command its electronic switch through an output line of one of its I/O ports. Nodes further down the loop can monitor the enable line, and also detect a fault from an upstream node or a downstream node and react accordingly. More specifically, at each node, an enable loop may pass through a series combination of a single-pole switch and a sense resistor in a block of circuitry labeled "switches" in FIG. 2. The switch may be selective opened or closed by the node according to whether or not the node detects a fault condition pertinent to the enable loop. The processor of the node provides a control signal to the switch by way of the I/O port facility of the node, as shown in the figure.

Figure 3:
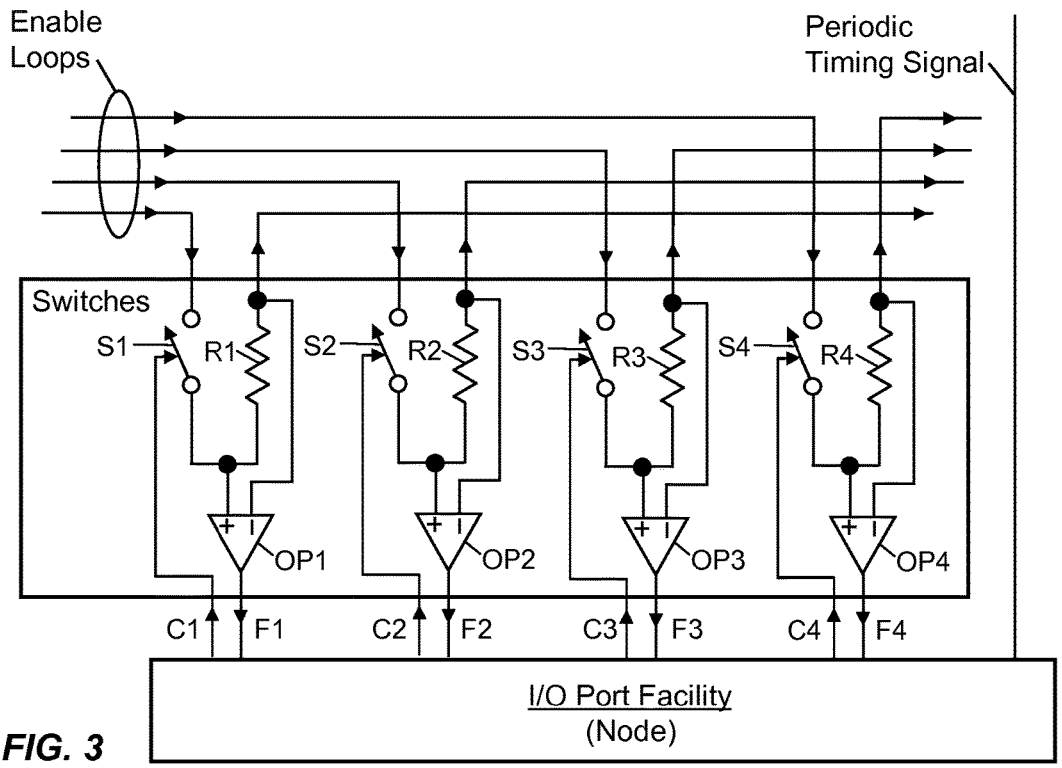
FIG. 3 shows an exemplary node switch block according to the present invention.

FIG. 3 shows an exemplary implementation of the switch block. Four enable loops are shown, which pass through four corresponding series combinations of switches S1-S4 and sense resistors R1-R4, respectively. If the node detects a fault condition, the node sends a corresponding command signal C1-C4 from its I/O port facility to the corresponding switch S1-S4 of the pertinent enable loop with a value that causes the switch to open (non-conducting); otherwise the node sends a command signal C1-C4 with a value that keeps the switch closed (conducting). Each switch S1-S4 may comprise a transistor, such as a MOSFET transistor. As the current of an enable loop passes through a node, it generates a voltage across the corresponding sense resistor R1-R4, which may be detected by a corresponding differential amplifier OP1-OP4 (e.g., "OP-Amps") that has inputs coupled to either side of the corresponding sense resistor R1-R4, as shown in the figure. The output of the corresponding differential amplifier OP1-OP4 provides a corresponding digital signal F1-F4 having a value of zero when no current is flowing in the enable loop (which indicates a fault condition), and a value of one when current is flowing in the enable loop (which indicates a normal, non-fault, condition). Signals F1-F4 are coupled to inputs of the node's I/O facility. Each differential amplifier OP1-OP4 may comprise zero-offset circuitry that causes it output to have a value of zero when the voltage difference across its inputs is zero. If not, such circuitry is known to the art, and can be readily added to the circuitry shown in the figure.

Figure 4:
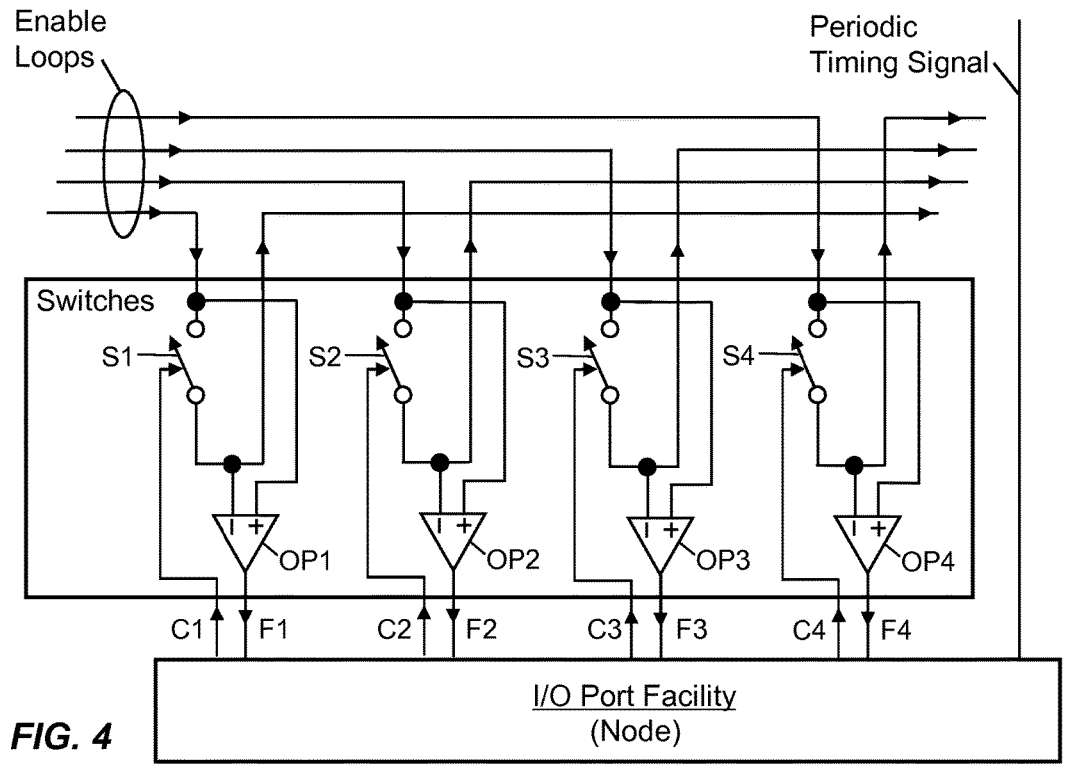
FIG. 4 shows another exemplary node switch block according to the present invention.

If the implementations for switches S1-S4 have sufficiently high on-state resistance, then switches S1-S4 may serve as the sense resistors R1-R4, respectively, This embodiment is shown in FIG. 4. As in the previous embodiment, four enable loops are shown, which pass through four corresponding switches S1-S4, respectively. If the node detects a fault condition, the node sends a corresponding command signal C1-C4 from its I/O port facility to the corresponding switch S1-S4 of the pertinent enable loop with a value that causes the switch to open (non-conducting); otherwise the node sends a command signal C1-C4 with a value that keeps the switch closed (conducting). Each switch S1-S4 may comprise a transistor, such as a MOSFET transistor. As the current of an enable loop passes through a node, it generates a voltage across the corresponding switch S1-S4, which may be detected by a corresponding differential amplifier OP1-OP4 (e.g., "OP-Amps") that has inputs coupled to either side of the corresponding switch S1-S4, as shown in the figure. The output of the corresponding differential amplifier OP1-OP4 provides a corresponding digital signal F1-F4 having a value of zero when no current is flowing in the enable loop (which indicates a fault condition), and a value of one when current is flowing in the enable loop (which indicates a normal, non-fault, condition). Signals F1-F4 are coupled to inputs of the node's I/O facility. Each differential amplifier OP1-OP4 may comprise zero-offset circuitry that causes it output to have a value of zero when the voltage difference across its inputs is zero. If not, such circuitry is known to the art, and can be readily added to the circuitry shown in the figure.

Figure 5:
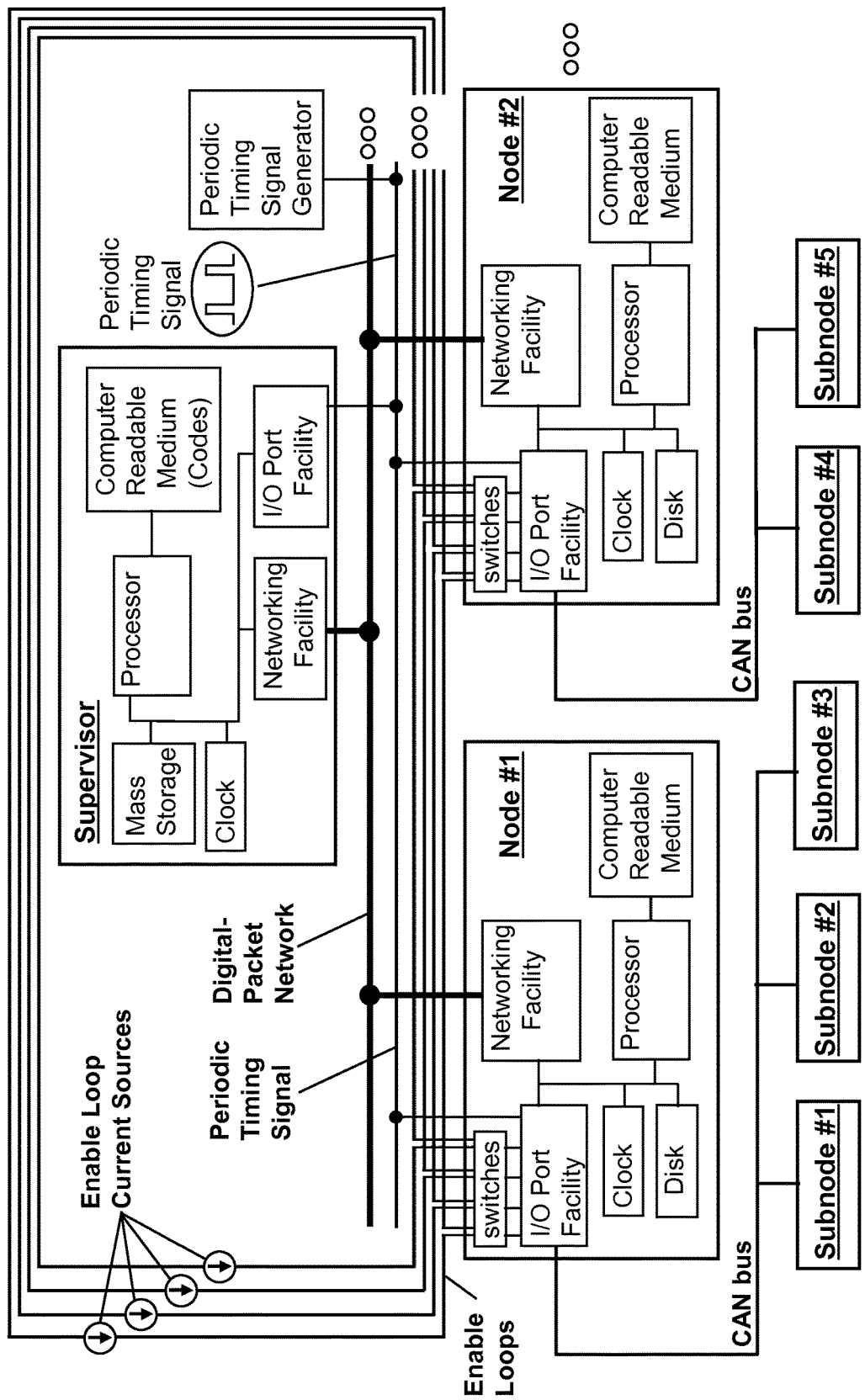
FIG. 5 shows another exemplary control system according to the present invention.

While the above example had the enables loops pass through the supervisor, such is not a requirement. Instead, the supervisor can monitor the faults detected by each node through the above-described status messages, which can provide more detailed information than the enable loop. The supervisor can also communicate fault information to nodes to cause the nodes to enter failsafe operating states. As such, in another implementation that is illustrated in FIG. 5, each enable loop is separate from the supervisor and is powered by a respective current source. Each enable loop comprises a current loop that passes through one or more of the nodes as a series circuit, with a respective current source coupled in series with the enable loop. Four enable loops are shown in FIG. 5, along with four current sources. As before, each enable loop may pertain to a different safety concern and/or control concern, and may pass through each node of the system, or only those nodes of the system which may detect a fault that is relevant to the concerns(s) pertaining to the control loop, or which may need to react to a fault condition detected by the enable loop. The implementation of the switches block shown in FIG. 5 may be the same as that shown in FIG. 3, or as that shown in FIG. 4.

Figure 6:
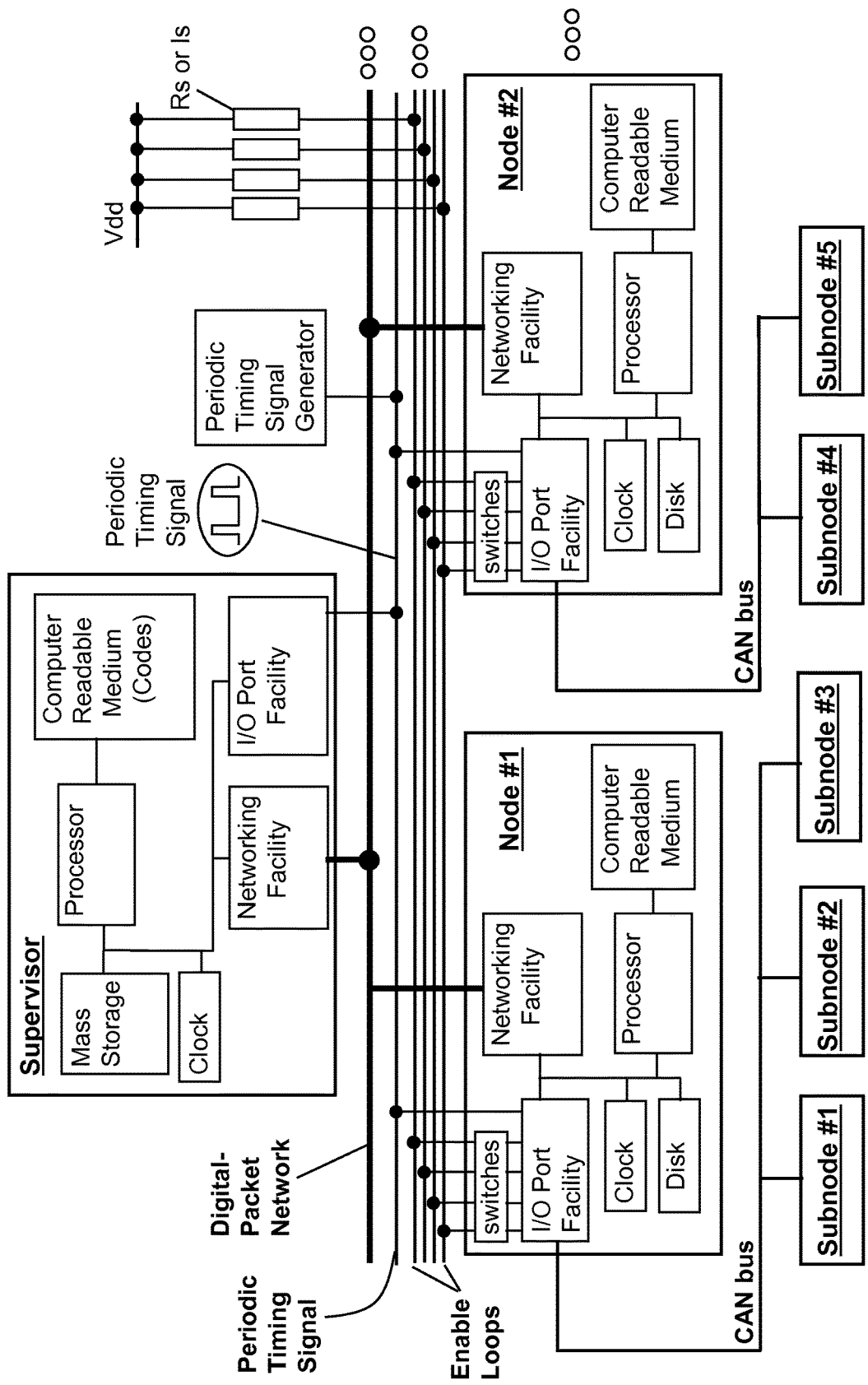
FIG. 6 shows another exemplary control system according to the present invention.

As another implementation, which is shown in FIG. 6, an enable loop may also be implemented as a wired NOR gate. In this configuration, a resistor Rs or current source Is supplies power to an enable line, and each node coupled to the enable line has its electronic switch coupled between the enable line and ground. This switch is in a block of circuitry labeled "switches" in FIG. 6, and may comprise a single-pole, single-throw switch. The enable line may also be coupled to an input line of the supervisor, but that is not necessary. The electronic switch may be selectively opened or closed by the node according to whether or not the node detects a fault condition pertinent to the enable loop. When a node detects no faults, it commands its electronic switch to the open position. When all the electronic switches are in the open position, the potential on the enable line goes to a logic high value (e.g., 3 or 5 volts). When a node detects a fault, it commands its electronic switch to the closed position, which causes the enable line to be grounded to a logic low value. The supervisor can detect a fault on the enable line by looking at the line's voltage level. In addition, all of the nodes coupled to the enable line can detect a fault on the enable line by looking at the line's voltage level, and can take appropriate action. The processor of the node provides a control signal to the switch by way of the I/O port facility of the node, as shown in the figure.

FIG. 7 shows an exemplary implementation of the switch block in FIG. 6. Four enable loops are shown, which are coupled to one terminal of a corresponding one of four switches S1-S4; the other terminals of switches S1-S4 are coupled to ground. If the node detects a fault condition, the node sends a corresponding command signal C1-C4 from its I/O port facility to the corresponding switch S1-S4 of the pertinent enable loop with a value that causes the switch to close (conducting); otherwise the node sends a command signal with a value that keeps the switch open (non-conducting). Each switch S1-S4 may comprise a transistor, such as a MOSFET transistor. The switch block may comprise a plurality of buffer inverters Inv1-Inv4 (e.g., four invertors) that have their inputs coupled to respective ones of the enable lines, and their outputs coupled to respective input lines of the node's I/O port facility. The output each of inverters Inv1-Inv4 provides a corresponding digital signal F1-F4 having a value of zero when the voltage on the enable line is high (which indicates a normal, non-fault condition), and a value near the digital supply voltage Vdd when the enable line is low (which indicates a fault condition). As an option, one or more enable loops may be coupled to the supervisor in the same way as a node, but this is not necessary. Instead, the supervisor can monitor the faults detected by each node through the above-described status messages, which can provide more detailed information than the enable loop. The supervisor can also communicate fault information to nodes, either in a direct form or an indirect form to cause the node to enter a failsafe condition.

Figure 10:
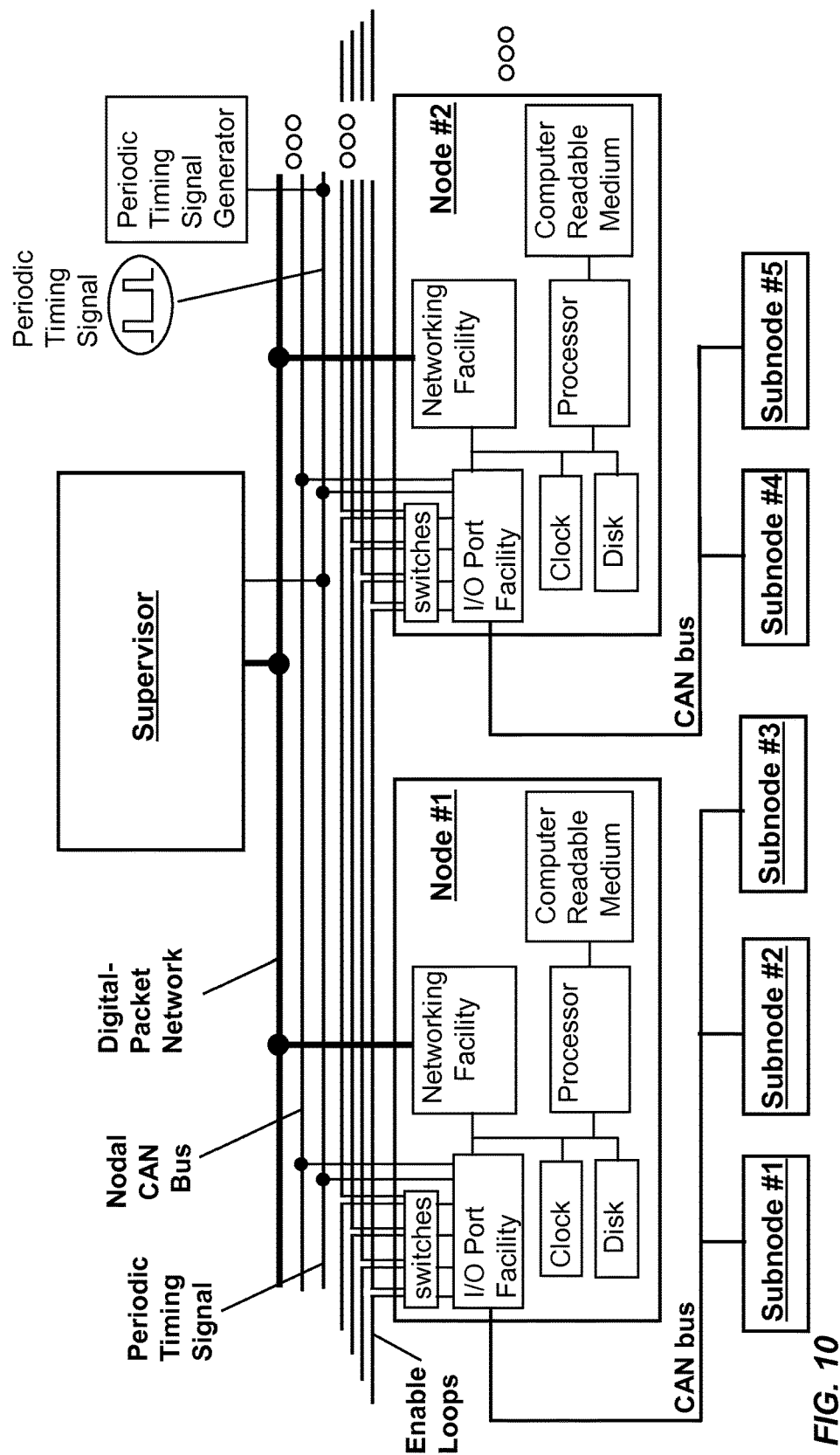
FIG. 10 another exemplary control system according to the present invention.

In the above embodiments, a CAN Bus (Control-Area Network bus) is provided for a node to communicate with its sub-nodes. In further embodiments, a "back-channel" communication channel is provided for peer-to-peer communication between the nodes over a CAN bus. An exemplary embodiment of such a back channel communication channel is illustrated in FIG. 10 by the "Nodal CAN Bus" shown in the figure. The Nodal CAN Bus is coupled to two or more nodes, which may be coupled to each such node through the node's I/O port facility. Any of the previously-described enable loops may be used in this embodiment. With the Nodal CAN Bus, one node may communicate directly to another node to coordinate their actions, if needed. For example, the collimator node (shown in FIG. 1) may send a message to the Beam Generator node (also shown in FIG. 1) over the Nodal CAN Bus to pause the generation of the treatment beam until the MLC 8 is in a desired position. The peer-to-peer communication of data packets between the nodes can typically be done at intervals of about 1 millisecond or less, which is shorter than the 10 millisecond communication interval of commands from the supervisor to the node. That is to say, data packets may be communicated amongst the nodes at a faster rate on the CAN Bus that data packets between the supervisor and an individual node. As another example, the couch node (also shown in FIG. 1) may have a device for detecting patient movement (for example, a camera), and may send a message to the Beam Generator node over the Nodal CAN Bus to indefinitely pause the generation of the treatment beam while it informs the supervisor of the patient's movement. The supervisor can then take responsive action at the next communication of commands to the nodes, which may involve sending commands to the system's components to place the components into a safe state for the patient and instructing the radiologist to reposition the patient.

Each of the above-described nodes and the supervisor can be implemented with any combination of hardware, firmware, and software that provides the above-described functions of the nodes and the supervisor. In view of this disclosure, one of ordinary skill in the art can construct embodiments of the nodes and the supervisor without undue experimentation. The use of the processors, computer-readable mediums, networking facilities, I/O port facilities, and clocks for the supervisor and nodes, as shown in the figures, simplifies the implementations since the implementation of the functions of the supervisor and the nodes can be more easily implemented in software. As is known in the art, the communication channels amongst the processor and the other aforementioned components is usually provided by an operating system. In this regard, the use of a real-time operating system can further simplify the implementations of the supervisor and the nodes by giving one of ordinary skill in the art more flexibility in writing the code that implements the functions of the supervisor and nodes. In this regard, the commonly used VxWorks operating system developed by Wind River Systems, now acquired by Intel, may be used.

Each of the above-described sub-nodes may be implemented with a conventional embedded processor (also called an "embedded system"). A typical embedded processor comprises a microprocessor, a flash memory (a non-volatile memory), volatile memory, a CAN Bus interface, and one or more I/O facilities, such as serial buses, A/D converters, and D/A converters. One example of an embedded processor is the Texas Instruments TMS320F2812 Digital Signal Controller (DSC). The flash memory stores the instructions for operating the microprocessor, and these instructions can readily be loaded into the flash memory by an external processor through the CAN Bus or another communication connection. These instructions can run on top of a "miniature" operating system for the Texas Instruments TMS-2812 DSP, which may comprise the Texas Instruments DSP-BIOS real-time multi-tasking kernel. The operating system is stored in the flash memory. A real-time operating system has the characteristic of completing a requested task in a deterministic manner within a predictable amount of time. The definition of a real-time operating system is well known to the art.

Figure 11:
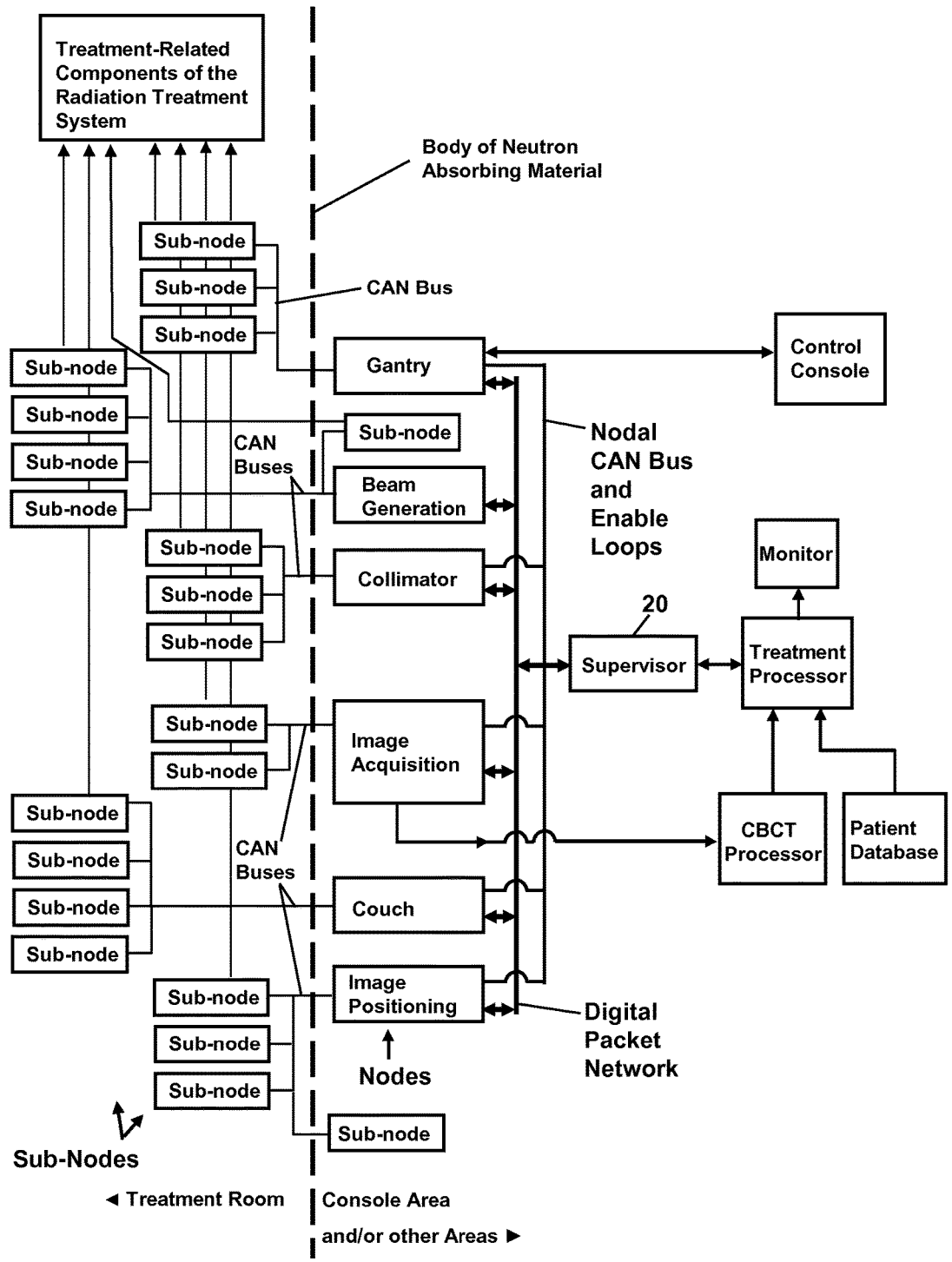
FIG. 11 shows an exemplary radiation treatment system according to another invention of disclosed by the present application.

As a result of conducting experiments with the invention using high-energy treatment beams, it was found that scattered neutrons were being generated by the target under these energy conditions and, as an unexpected result, the scattered neutrons were reaching the supervisor, nodes, and sub-nodes of the system and affecting the operation of the system. These results were not found for low to moderate energy treatment beams. In response, applicants developed the following further inventions for high energy treatment beam applications (but the further inventions may be used for low and moderate energy treatment beams as well). As a first further invention, as illustrated in FIG. 11, the supervisor, the nodes, and networking equipment associated with the Digital Packet Network are located outside of the treatment room, and the sub-nodes are located within the treatment room along with the treatment-related components of the radiation treatment system. In some cases, it is also possible to locate some of the sub-nodes outside of the treatment room. Because of the radiation generated by the treatment system, the walls, ceiling, floor, and doors of the treatment room comprises materials that absorb radiation. As it turns out, these materials also absorb neutrons. Materials commonly used for this absorption purpose include concrete and lead. These materials absorb neutrons to a greater degree than the common materials used in dry wall construction (e.g., gypsum). Borated polyethylene is also effective for absorbing neutrons. An appropriate thickness of lead, concrete or borated polyethylene can absorb neutrons to a such a degree that the neutron flux density (the number of neutrons per second per square area) reaching the equipment outside the treatment room is reduced by a factor of ten or more, thereby effectively attenuating the neutrons so that the chances of a neutron-upset event in the equipment is negligible. As such, for high-energy treatment applications, it is beneficial to dispose a body of neutron-absorbing material (e.g., such as in a wall, door, ceiling, etc.) between the equipment and the treatment-related components of the system (particularly the radiation-producing components) and the above-noted components of the control system (e.g., supervisor, nodes, and optionally some sub-nodes and ancillary control logic), where the body of neutron-absorbing material reduces the neutron flux density by a factor of ten or more.

As a further invention, the supervisor and nodes may be located in the treatment room, but with a body of neutron-absorbing material disposed between them and at least the neutron emitting treatment-related components.

Figure 12:
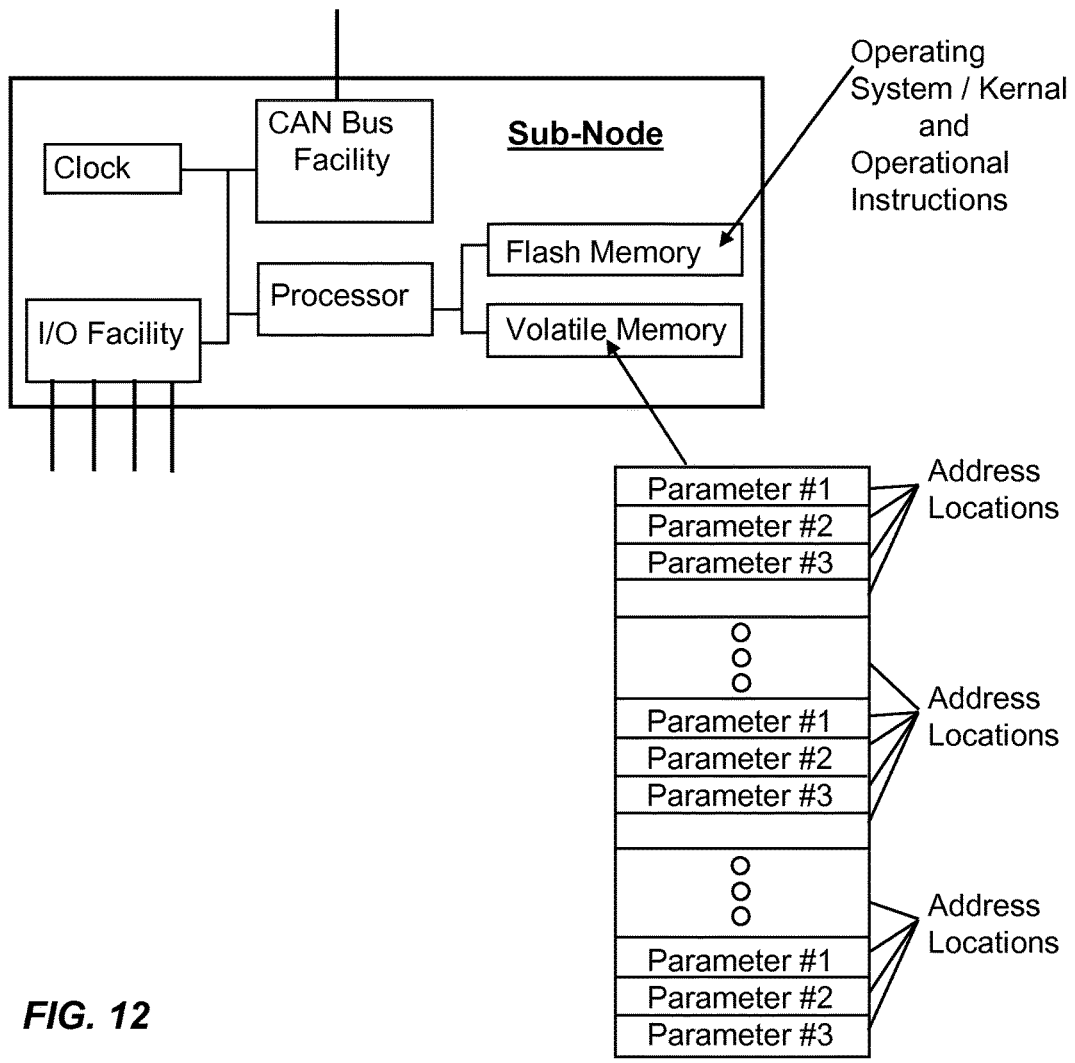
FIG. 12 shows an exemplary sub-node that may be used in a radiation treatment system according to yet another invention of disclosed by the present application.

As yet a further invention, a sub-node may comprise a processor, a flash memory (which is a non-volatile memory) coupled to the processor and that holds the operating system (e.g., kernel) for the sub-node and the instructions for directing the processor, and a volatile memory for storing one or more parameters that the sub-node uses in its operations. An exemplary sub-node is shown in FIG. 12. Further, each parameter is stored at three or more different memory locations of the volatile memory at three or more respective different memory addresses. A parameter is an item of data that the sub-node uses in its operation, and the value of the parameter can change with time, and can be modified by the sub-node itself or by the node that controls the sub-node. Whenever the sub-node needs to use such a parameter, it has instructions stored on the flash memory that directs the sub-node's processor to read the three or more locations of the volatile memory for the parameter, and directs the data processor to compare the three or more values to determine if at least two of the read locations have the same value, and preferably if a majority of the read locations have the same value. If two or more are the same, or more preferably if a majority are the same, the instructions direct the data processor to use the same value. If none of the three or more read locations have the same value, or more preferably if a majority of the read locations do not have the same value, then the instructions direct the data processor to send an error message to the node for the sub-node that informs the node of the lack of a good value for the parameter and a request for a fresh copy of the parameter value. Whenever the nodes sends a new parameter value to the sub-node, the sub-node has instructions stored on the flash memory that direct the sub-node's processor to write the received value of the parameter to the three or more locations in the volatile memory that are allocated to store the parameter. It is noted that flash memory is less sensitive to some forms of radiation (such as photon and neutron emissions) compared to static semiconductor random-access memory (SRAM) and dynamic random-access memory (DRAM), so that these stored instructions are relatively safe against radiation exposure and neutron compared to the parameters stored in the volatile memory. However, the volatile memory a larger number of rewrites of the memory locations for the parameters before the memory fails (in other words, flash memories have the disadvantage of a limited number of write operations to a memory location).

Despite all of the above-described complexity, the control architecture can be implemented by low-cost, off-the-shelf communication protocol components (UDP over Ethernet) for which many easy-to-use development tools are available.

In summary, at a high level, the supervisor maintains a top-level view over all activities and motions in the system. The supervisor knows the entire treatment plan and is able to break it into 10 mSec trajectory steps for all axes (mechanical parameters). Generally speaking, the treatment plan held by supervisor 20 comprises a coordination of the operation of the treatment-related components of radiation treatment system 10 over a selected period of time, where the coordination can be described by sets of action orders to the nodes, one set per node. At a mid-level, numerous nodes (each with processors) manage the information unique to each subsystem; these nodes communicate directly with the supervisor over a digital packet network (e.g., a local Ethernet network). Also, a back channel communication channel is available for peer-to-peer nodal communication over a CAN bus. Each node need only know what it has to do for the next 20 and 30 mSec (the next two active pulses on the periodic timing signal); it does not need to know the entire treatment plan. At a low level, numerous sub-nodes (each with control logic and/or processors) manage information unique to a few components (e.g. power supplies, steering coils, tuning magnets). Sub-nodes communicate directly to their controlling node; there is no peer-to-peer communication.

Advantages Compared to Prior Art Systems.

The distributed structure of the present invention approach allows the software to be compartmentalized in a manner that does not force software engineers to become whole system experts. It is easier to manage a software development team in which people can know just a subsystem or component instead of the whole system. The use of off-the-shelf networking technologies (e.g., Ethernet and UDP) coupled with the backup safety enable loop technology allows the engineers to develop and modify the system in a rapid and safe manner—engineers will not be re-inventing the wheel. Since the supervisor understands the acceleration profiles of all axes, it is able to break an entire plan into steps that coordinate according to the speed of the slowest axis. Because of this, there will no longer be treatments in which the beam is held while mechanical motion catches-up (such as in cases where the X-ray beam is held while the MLC leaves catch-up to the plan). Since the supervisor knows where every mechanical axis is, multiple axes can move at the same time (in prior systems, to avoid collisions, just a limited set of axes can move at the same time). Since the supervisor coordinates beam, motion and imaging, it is easier to create advanced techniques in which multiple things occur at the same time ("dynamic treatments"). Examples include: (1) RapidArc and Large Field IMRT, (2) Interleaved MV treatment & KV imaging, (3) fluoroscopy-guided gating treatments (prior to treatment, KV fluoroscopy images are correlated with the respiratory-induced motion of an Infra-red reflector; this correlation allows subsequent accurate beam gating in accordance with organ motion), (4) Dynamic tracking—these type of plans involve moving the system in accordance with patient motion (e.g., moving the MLC leaves as the patient breathes).

Any recitation of "a", "an", and "the" is intended to mean one or more unless specifically indicated to the contrary.

The computer-readable medium and memory devices described herein are preferably tangible and/or non-transitory.

The terms and expressions which have been employed herein are used as terms of description and not of limitation, and there is no intention in the use of such terms and expressions of excluding equivalents of the features shown and described, it being recognized that various modifications are possible within the scope of the invention claimed.

Moreover, one or more features of one or more embodiments of the inventions may be combined with one or more features of other embodiments of the inventions without departing from the scope of the inventions.

While the present inventions have been particularly described with respect to the illustrated embodiments, it will be appreciated that various alterations, modifications, adaptations, and equivalent arrangements may be made based on the present disclosure, and are intended to be within the scope of the inventions and the appended claims.

What is claimed is:

1. A radiation treatment system for providing radiation to a patient, the system comprising:
 a plurality of treatment-related components that coordinate to provide the radiation to the patient according to a treatment plan;
 a digital packet network;
 a supervisor control entity communicably coupled to the digital packet network and having the treatment plan; and
 a plurality of nodes, each node coupled to the digital packet network and controlling one or more of the treatment-related components, each node controlling a different set of one or more of the treatment-related components, wherein the plurality of nodes implement the treatment plan for the patient,
 wherein the supervisor control entity is configured to:
  periodically communicate commands to the nodes over the digital packet network during implementation of the treatment plan, each of the commands to a node in the plurality of nodes specifying one or more actions to be performed by the node at a particular time point in the treatment plan; and
  provide, during implementation of the treatment plan, a periodic timing signal to the nodes so as to synchronize the one or more actions performed by the nodes, wherein each node is configured to perform, in response to receipt of a next active pulse of the periodic timing signal, an action from the one or more actions specified in a command previously received from the supervisor control entity.

2. The radiation treatment system of claim 1, wherein the nodes are configured to periodically provide status information to the supervisor control entity over the digital packet network.

3. The radiation treatment system of claim 1, wherein the supervisor control entity is configured to communicate, to the nodes, commands that each comprise action orders for two or more distinct points in time.

4. The radiation treatment system of claim 3, wherein a first node of the plurality of nodes is configured to receive a first command including:
 a first action order for a first time point, and
 a second action order for a second time point, the second time point being subsequent to the first time point.

5. The radiation treatment system of claim 4, wherein the first node is further configured to receive a second command after receiving the first command, the second command including:
 the second action order for the second time point, and
 a third action order for a third time point, the third time point being subsequent to each of the first and second time points.

6. The radiation treatment system of claim 4, wherein the first node is configured to send a message packet to the supervisor control entity over the digital-packet network when the first node has not received a command from the supervisor control entity within a selected period of time.

7. The radiation treatment system of claim 1, wherein at least one node controls a multi-leaf collimator of the radiation treatment system, controls a linear accelerator of the radiation treatment system, or controls a gantry of the radiation treatment system, or any combination thereof.

8. The radiation treatment system of claim 1, further comprising at least one sub-node, wherein the at least one sub-node controls at least one aspect of a treatment-related component and receives directions from a node among the plurality of nodes.

9. The radiation treatment system of claim 1, wherein the plurality of treatment-related components are disposed within a treatment room, and wherein the supervisor control entity and at least one node from the plurality of nodes are disposed outside of the treatment room, and wherein a body of material that absorbs neutrons to a greater degree than gypsum is disposed between the supervisor control entity and the plurality of the treatment-related components.

10. The radiation treatment system of claim 9, wherein said body is further disposed between said at least one node from the plurality of nodes and said plurality of the treatment-related components, the body of neutron-absorbing material reducing the neutron flux density passing through itself by a factor of ten or more.

11. A method for providing radiation to a patient using a radiation treatment system that includes a supervisor control entity communicably coupled to a plurality of nodes via a digital packet network, each node controlling one or more of a plurality of treatment-related components that coordinate to provide the radiation to the patient according to a treatment plan, the method comprising:
 periodically communicating, by the supervisor control entity, commands to the plurality of nodes over the digital packet network during implementation of the treatment plan, each of the commands to a node in the plurality of nodes specifying one or more actions to be performed by the node in the plurality of nodes at a particular time point in the treatment plan, wherein each node controls a different set of one or more of the treatment-related components, and wherein the plurality of nodes implement the treatment plan for the patient; and
 provide, during implementation of the treatment plan, a periodic timing signal to the nodes so as to synchronize the one or more actions performed by the nodes, wherein each node is configured to perform, in response to receipt of a next active pulse of the periodic timing signal, an action from the one or more actions specified in a command previously received from the supervisor control entity.

12. The method of claim 11, further comprising:
 periodically providing, by the nodes, status information of the nodes to the supervisor control entity over the digital packet network.

13. The method of claim 11, further comprising:
 communicating, by the supervisor control entity to the nodes, commands that each comprise action orders for two or more distinct points in time.

14. The method of claim 13, further comprising:
 receiving, by a first node of the plurality of nodes, a first command including:
  a first action order for a first time point, and
  a second action order for a second time point, the second time point being subsequent to the first time point.

15. The method of claim 14, further comprising:
 receiving, by the first node of the plurality of nodes, a second command after receiving the first command, the second command including:
  the second action order for the second time point, and a third action order for a third time point, the third time point being subsequent to each of the first and second time points.

16. The method of claim 14, further comprising:
sending, by the first node, a message packet to the supervisor control entity over the digital-packet network when the first node has not received a command from the supervisor control entity within a selected period of time.

17. The method of claim 11, wherein at least one node of the plurality of nodes controls a multi-leaf collimator of the radiation treatment system, controls a linear accelerator of the radiation treatment system, or controls a gantry of the radiation treatment system, or any combination thereof.

18. The method of claim 11, further comprising:
receiving, by at least one sub-node, directions from a node of the plurality of nodes, wherein the at least one sub-node controls at least one aspect of a treatment-related component.

19. The method of claim 11, wherein the plurality of treatment-related components are disposed within a treatment room, and wherein the supervisor control entity and at least one node of the plurality of nodes are disposed outside of the treatment room, and wherein a body of material that absorbs neutrons to a greater degree than gypsum is disposed between the supervisor control entity and the plurality of the treatment-related components.

20. The method of claim 19, wherein said body is further disposed between the least one node of the plurality of nodes and said plurality of the treatment-related components, the body of neutron-absorbing material reducing the neutron flux density passing through itself by a factor of ten or more.

* * * * *

UNITED STATES PATENT AND TRADEMARK OFFICE
CERTIFICATE OF CORRECTION

PATENT NO. : 10,258,812 B2
APPLICATION NO. : 14/631617
DATED : April 16, 2019
INVENTOR(S) : Andres Graf et al.

Page 1 of 1

It is certified that error appears in the above-identified patent and that said Letters Patent is hereby corrected as shown below:

On the Title Page

Item (72), Line 2, delete "Zofingen (CN);" and insert -- Zofingen (CH); --, therefor.

Signed and Sealed this
Fourteenth Day of May, 2019

Andrei Iancu
*Director of the United States Patent and Trademark Office*